United States Patent

Kaneko et al.

[11] Patent Number: 5,503,728
[45] Date of Patent: Apr. 2, 1996

[54] CARBON SENSOR ELECTRODE AND PROCESS FOR PRODUCING THE SAME

[75] Inventors: Hiroko Kaneko, Tsukuba; Akira Negishi, Matsudo; Ken Nozaki, Tsukuba, all of Japan

[73] Assignee: Agency of Industrial Science and Technology, Tokyo, Japan

[21] Appl. No.: 317,816

[22] Filed: Oct. 4, 1994

Related U.S. Application Data

[63] Continuation-in-part of Ser. No. 117,696, Sep. 8, 1993, abandoned.

[30] Foreign Application Priority Data

| Sep. 9, 1992 | [JP] | Japan | 266706 |
| Sep. 9, 1992 | [JP] | Japan | 266707 |
| Oct. 5, 1993 | [JP] | Japan | 5-273036 |

[51] Int. Cl.$^6$ ............... G01N 27/26; C25B 11/00
[52] U.S. Cl. ............ 204/290 R; 204/294; 204/418; 204/415; 204/282; 204/402; 204/403
[58] Field of Search ............... 204/282, 290 R, 204/294, 402, 403, 415, 418, 419

[56] References Cited

U.S. PATENT DOCUMENTS

| 4,439,303 | 3/1984 | Cocchi | 204/294 |
| 4,756,813 | 7/1988 | Stanley | 204/294 |
| 5,174,883 | 12/1992 | Martin et al. | 204/400 |
| 5,272,087 | 12/1993 | El Murr et al. | 204/403 |
| 5,281,319 | 1/1994 | Kaneko et al. | 204/294 |

FOREIGN PATENT DOCUMENTS

| 1-250854A | 10/1989 | Japan. |
| 5-18928A | 1/1993 | Japan. |

*Primary Examiner*—Bruce F. Bell
*Attorney, Agent, or Firm*—Spencer & Frank

[57] ABSTRACT

A carbon electrode is dipped in a solution containing a reactive substance, and the carbon electrode impregnated with the solution is covered with an insulating tubular member; or a solution containing a reactant is poured into an insulating tube, and a carbon electrode is inserted into the tube; whereby the reactant is made coexistent in the periphery of the carbon electrode. Alternatively, a reactive substance such as an active enzyme and graphite particles or activated carbon particles are mixed with a liquid and dispersed therein to prepare a thoroughly wetted paste. The paste is introduced by means of an extruding mechanism such as a syringe into an insulating tubular member in which a bundle of many thin carbon rods as a lead is inserted. Thus, a carbon sensor electrode is produced. Alternatively, a first carbon electrode that has been dipped in an active enzyme or an enzyme-like reactive substance solution is disposed in a wet condition in a cylindrical ion permeable membrane. To prevent the enzyme or enzyme-like reactive substance in the electrode from becoming deactivated with the passage of time, a preliminary electrode is further inserted into the insulating tubular member, whereby the potential can be kept to be oxidation or reduction potential so as to ensure a constant sensor life. A fresh electrode surface having the active enzyme or enzyme-like reactive substance can be easily obtained by cutting or snapping off a tip portion of the sensor including the insulating tubular member.

16 Claims, 7 Drawing Sheets

CARBON SENSOR ELECTRODE AND PROCESS FOR PRODUCING THE SAME

CROSS-REFERENCE TO RELATED APPLICATION

The present application is a continuation in part application of U.S. application Ser. No. 08/117,696, filed on Sep. 8, 1993, now abandoned.

BACKGROUND OF THE INVENTION

1. Field of the Invention

The present invention relates to a carbon sensor electrode for use in various sensors such as electrochemical detectors, sensors for environment analysis, sensors for pathological examinations, and probe electrodes for detection of in vivo conditions. It also relates to a process for producing the carbon sensor electrode.

2. Description of the Prior Art

Among major fields of electrochemical measurement is simple rapid analysis relying for detection on sensors that have shown prompt progress in recent years. Since this method is highly selective and permits high sensitivity measurement, it has found extensive use in the analysis and evaluation of clinical samples or environmental samples containing minute quantities of ingredients to be determined and having numerous compounds coexistent therein.

In recent years, it has become crucial to obtain information on such particular substances in vivo and in situ locally in a biological system by use of a sensor electrode which can detect these substances with high sensitivity and rapidity. Acquisition of to that information requires the use of an easily producible disposable electrode, or the use of a sensors from which a fresh electrode surface can be easily obtained and which can selectively measure a particular substance in vivo.

Such measuring electrodes which have been studied and put to practical use include pH meters which measure hydrogen ions; ion sensors which detect inorganic ions such as sodium ions; sensors comprising carbon fibers or glassy carbon chemically modified with complexes or organic matters on the surfaces thereof; various enzyme sensors such as glucose sensors prepared by mixing enzymes such as glucose oxidase with the paste of a carbon paste electrode, and coating the mixture with an ion permeable membrane; and biosensors holding metabolites from immune mechanisms.

However, most sensors including chemically modified sensors, enzyme sensors and biosensors, except for pH meters and inorganic ion sensors, are defective in that they cannot withstand long-term use and their lives are short. Thus, a desire has been strong for the development of long life sensor electrodes preferred for use in sensors excluding pH meters and inorganic ion sensors.

The requirements for sensor electrodes include, for instance, (i) a large potential window and a low blank current, (ii) a highly reproducible, repeatable reaction of a particular substances, (iii) an active electrode reaction, (iv) no differences among individual electrode characteristics, (v) little content of impurities, thus not interfering in an electrode reaction, and (vi) ease of handling and pretreatment.

We, the present inventors, previously found that a probe electrode using the lead of a mechanical pencil which is a thin rod of carbon (Japanese Patent Application Laying-open No. 250854/1989) could be used as a material for a sensor electrode fulfilling most of the above-mentioned requirements, and that some carbon fibers could be used in measuring electrodes. As is well known, that mechanical pencil lead is a composite carbonaceous material comprising naturally occurring graphite and an organic binder.

We attempted to solve the aforementioned problem of life with the conventional sensors by using the composite carbonaceous material. Prior to the filing of the present application, we proposed a sensor preferred as a chemically modified sensor, an enzyme sensor or a biosensor (Japanese Patent Application Laying-open No. 18928/1993). Since micropores are formed during the production of the composite carbonaceous material, this previously proposed sensor takes advantage of the micropores to achieve increased conductivity. It also has controlled pore sizes, thereby making a sensor substrate usable for long periods. In this sensor, moreover, the surface and internal communicating micropores of a porous carbon thin wire which is the sensor substrate are impregnated, adsorbed or chemically modified with a reactant such as an enzyme, a metal complex, an organic substance or a metabolite, whereby the desired reactant is held inside or on the surface.

This electrode is a carbon sensor electrode capable of detecting particular substances, and has the following characteristics:

1. It provides a cell-scale carbon microsensor electrode which can apply an electric current, an electric voltage or a mechanical stimulus to a living system.

2. It does not poison the measuring system (if it remains in vivo, it is safe), and it can be used for testing foods.

3. It has a mechanical strength enough high to be stuck into the body or food, permitting the electrochemical detection of a very fine (a very small amount of) portion.

4. It has minimally fluctuating characteristics, offers reproducible data, and enables reliable measurement.

5. It does not require special pretreatments, and polishing is sufficient for its stable measurement of an electrode reaction.

6. It is low-priced and disposable.

However, this electrode is disadvantageous in that its poor carbon wettability may pose difficulty in impregnating a reactive substance into the resulting micropores.

The living system where the carbon sensor electrode is used for measurement contains large amounts of adsorbable organic substances such as proteins and lipids in a coexistent fashion. Once adsorbed to the carbon surface of the sensor, these organic matters are not easily removable unless oxidized. If the carbon sensor electrode is to be reused, therefore, care should be taken to discard the electrode portion after each use, or to break off the used electrode portion. In clinical examinations, the reuse of the same sensor that was used on other samples may cause errors for the above reason. Thus, a carbon sensor electrode having the used electrode portion disposable is desired. The requirements for a carbon sensor and a carbon sensor electrode of a construction with disposable characteristics are as follows:

(1) Carbon compatible with the body constitutes an electrode.

(2) The carbon material has high activity as an electrode.

(3) A reactant such as an enzyme can be held active in the sensor.

(4) A used electrode portion can be snapped or cut off.

(5) The price is low enough for disposable use.

A disposable carbon sensor electrode should fulfill at least the above five requirements. For this purpose, a carbon sensor electrode is desirable in which the desired reactant such as an enzyme, a metal complex or a metabolite is always easily made to exist on the surface of the electrode and which can be produced economically. In order for the carbon sensor electrode to be usable for long periods, it is important that the requirement (3), in particular, be fulfilled.

Furthermore, there are some reactants which become deactivated by the oxygen in the air. In this case, to solve this problem and have the carbon sensor ready for measurement where necessary, the important task is to prepare a redox type carbon sensor electrode whose potential is kept to be oxidation or reduction potential so that the reactive substance may be kept active.

In addition to the carbon sensor electrode using the composite carbon material (lead of a mechanical pencil), a preferred sensor electrode is conceivable which is a commercial carbon paste electrode prepared by mixing fine carbon particles with a liquid. Such a commercially available carbon paste electrode has a mixture of carbon particles for electrode and a liquid held at the tip of the electrode, or may have a reactant additionally mixed. Some of such carbon paste electrodes may be used as disposable sensors. The carbon paste electrode, however, must be handmade for each use, thus often causing delicate differences in the mixing state or in the electrode surface every time it is prepared.

The object of the present invention, therefore, is to provide the construction of a carbon sensor electrode satisfying the above-described requirements, and a process for producing the carbon sensor electrode.

SUMMARY OF THE INVENTION

A carbon sensor electrode in accordance with the present invention comprises an insulating tubular member, a carbon electrode consisting of a bundle of many linear thin carbon member and being disposed in the insulating tubular member, a solution containing a reactive substance which reacts chemically with a composition being to be measured by the carbon sensor electrode, and being held between the carbon electrode and the insulating tubular member as well as between each linear thin carbon members.

A process for producing a carbon sensor electrode in accordance with the present invention comprises dipping a carbon electrode consisting of a bundle of many linear thin carbon member in a solution containing a reactive substance which reacts chemically with a composition which is measured by the carbon sensor electrode, and covering the carbon electrode with an insulating tubular member with the solution being held between the carbon electrode and the insulating tubular member as well as between each carbon members; or comprises pouring a solution containing a reactive substance which reacts chemically with a composition being to be measured by the carbon sensor electrode into an insulating tubular member, and inserting a carbon electrode consisting of a bundle of many linear thin carbon members into the insulating tubular member to hold the solution between the carbon electrode and the insulating tubular member as well as between each carbon members.

The linear thin carbon member is preferably a carbon fiber or thin carbon rod. In this case that the first carbon electrode consists of a bundle of many linear thin carbon members, the carbon sensor electrode can further obtain the following constitution and the effect therefrom. The bundle of many linear thin carbon members may be separated at least two bundle groups at its basal part where is out of the solution. Each end of the separated bundle groups of the carbon members may be connected to power source so that each of ends is applied different electric potential respectively. By this constitution, the carbon sensor electrode can amplify its measuring current to obtain higher sensitivity on measuring.

The insulating tubular member is preferably an insulating tube or an insulating sheet.

The reactive substance is a substance which reacts chemically with a composition which is measured by the carbon sensor electrode of the present invention. In this specification, the term "chemical reaction" includes "electrochemical reaction".

Examples of the reactive substance are organic substances including active enzymes, nitrogen metabolites such as uric acid, amino acid metabolites, neurotransmitters such as dopamine, vitamins, organic acids such as acetic acid or citric acid, amines, alcohols, and medicines such as anesthetics; complex ions; inorganic acids such as hydrochloric acid or sulfuric acid; alkalis such as ammonia or hydroxides; salts of the inorganic acids and alkalis; soluble gases such as oxygen, chlorine or nitrogen oxides; mixtures of any of these; and substances containing any of them.

To prevent the reactive substance from draining into the bulk solution, the reactive substance may be held in place with carriers such as vaseline, paraffin, oil, glycerin, agar or gelatin.

Furthermore, the solution mixed with the carrier is further mixed with a fine carbon material to produce a paste-like solution(a carbon paste), thus the carbon paste is filled between the carbon electrode and the insulating tubular member as well as between each linear thin carbon members. By this constitution, the carbon sensor electrode can enhance its sensitivity.

The tip opening of the insulating tubular member may be sealed with an ion permeable membrane, an ion exchange membrane or a dialysis membrane in order to prevent the reactive substance from draining into the bulk solution.

Moreover, a reaction solution feeding device for feeding the solution containing the reactive substance may be connected with a base portion of the insulating tubular member so that a fresh reactive substance can be constantly fed to the tip of the electrode. A solution injector or a pump capable of fine adjustment for a slow speed may be used as the reaction solution feeder.

A carbon sensor electrode using a carbon paste in accordance with the present invention comprises an insulating tubular member, and a carbon electrode consisting of a carbon paste filled inside the insulating tubular member, wherein the carbon paste comprises at least a fine carbon material, a carrier, and a reactive substance which reacts chemically with a composition which is measured by the carbon sensor electrode.

A process for producing the carbon sensor electrode using a carbon paste in accordance with the present invention comprises homogeneously mixing at least a fine carbon material, a solution containing a reactive substance which reacts chemically with a composition being to be measured by the carbon sensor electrode, and a carrier with a dispersing medium to prepare a carbon paste, and placing the carbon paste inside a insulating tubular member.

The fine carbon material is preferably selected from activated carbon particles, graphite particles, amorphous carbon part icles, short carbon fibers, and mixtures of these.

The carrier is preferably at least one of vaseline, glycerin, oil, paraffin, agar and gelatin.

The carbon paste preferably contains a reactive substance. Examples of the reactive substance are organic substances including active enzymes, nitrogen metabolites such as uric acid, amino acid metabolites, neurotransmitters such as dopamine, vitamins, organic acids such as acetic acid or citric acid, amines, alcohols, and medicines such as anesthetics; complex ions; inorganic acids such as hydrochloric acid or sulfuric acid; alkalis such as ammonia or hydroxides; salts of the inorganic acids and alkalis; soluble gases such as oxygen, chlorine or nitrogen oxides; mixtures of any of these; and substances containing any of them.

The dispersing medium for mixing the reactive substance and the fine carbon material is preferably either an aqueous solution, an organic solvent, or a mixture of these.

The insulating tubular member is preferably an insulating tube or an insulating sheet.

Furthermore, the tip opening of the insulating tubular member may be sealed with an ion permeable membrane, an ion exchange membrane or a dialysis membrane.

Moreover, a carbon paste feeder capable of continuously feeding the carbon paste may be connected with a base end portion of the insulating tubular member so that a fresh sensor end can be constantly obtained.

A redox type carbon sensor electrode in accordance with the present invention comprises an insulating tubular member, a cylindrical ion permeable membrane being disposed in the insulating tubular member, a first carbon electrode being disposed in the cylindrical ion permeable membrane, a solution containing a reactive substance being held on the first carbon electrode as well as between the first carbon electrode and the cylindrical ion permeable membrane, and a second carbon electrode being disposed between the insulating tubular member and the cylindrical ion permeable membrane.

A process for producing a redox type carbon sensor electrode in accordance with the present invention comprises, dipping a first carbon electrode in a solution containing a reactive substance which reacts chemically with a composition being to be measured by the carbon sensor electrode, disposing the first carbon electrode in the solution in a cylindrical ion permeable membrane to hold the solution in the first carbon electrode as well as between the first carbon electrode and the cylindrical ion permeable membrane, disposing the cylindrical ion permeable membrane including the first carbon electrode and the solution in an insulating tubular member, and disposing a second carbon electrode between the insulating tubular member and the cylindrical ion permeable membrane.

Another process for producing a redox type carbon sensor electrode in accordance with the present invention comprises, pouring a solution containing a reactive substance which reacts chemically with a composition which is measured by the carbon sensor electrode into a cylindrical ion permeable membrane, inserting a first carbon electrode into cylindrical ion permeable membrane to hold the solution between the carbon electrode and the ion permeable membrane, disposing the cylindrical ion permeable membrane with the first carbon electrode and the solution into a insulating tubular member, and disposing a second carbon electrode between the insulating tubular member and the cylindrical ion permeable membrane.

The first carbon electrode may be composed of one member selected from the group consisting of a twisted carbon yarn of carbon fibers, a thin carbon rod, a bundle-form carbon composed of twisted carbon yarns or thin carbon rods, and a carbon cloth of twisted carbon yarns.

Here, in the case that the first carbon electrode consists of a bundle of many linear thin carbon members, the carbon sensor electrode can further obtain the following constitution and the effect therefrom. The bundle of many linear thin carbon members may be separated at least two bundle groups at its basal part where is out of the solution. Each end of the separated bundle groups of the carbon members may be connected to power source so that each of ends is applied different electric potential respectively. By this constitution, the carbon sensor electrode can amplify its measuring current to obtain higher sensitivity on measuring.

The second carbon electrode may be composed of one member selected from the group consisting of a twisted carbon yarn of carbon fibers, a thin carbon rod, a bundle-form carbon composed of twisted carbon yarns or thin carbon rods, and a carbon cloth of twisted carbon yarns.

The insulating tubular member may be an insulating tube or an insulating sheet rolled into a tubular form.

The reactive substance which reacts chemically with a composition which is measured by the carbon sensor electrode may contain a substance such as an active enzyme, a metabolite, complex ions, an acid, an alkali or a dissolved gas.

The reactive substance may be coexistent with a retaining material such as vaseline, glycerin, oil, agar or gelatin so as not to drain immediately into the bulk solution.

In the constitution mentioned above, an ion permeable membrane may be attached to a front end of the tubular member so that the reactive substance may not immediately drain into the bulk solution.

Also, a reaction solution push-out mechanism capable of constantly feeding a reaction solution may be attached to the insulating tubular member.

And also, an ion exchange membrane, an ion permeable membrane of cellophane or the like, a sintered glass membrane, or an insulating ion permeable membrane of a Teflon filter paper or the like may be used as the ion permeable membrane.

The above and other objects, effects, features and advantages of the present invention will become more apparent from the following description of embodiments thereof taken in conjunction with the accompanying drawings.

DETAILED DESCRIPTION OF PREFERRED EMBODIMENTS

Embodiment 1

Figure 1:
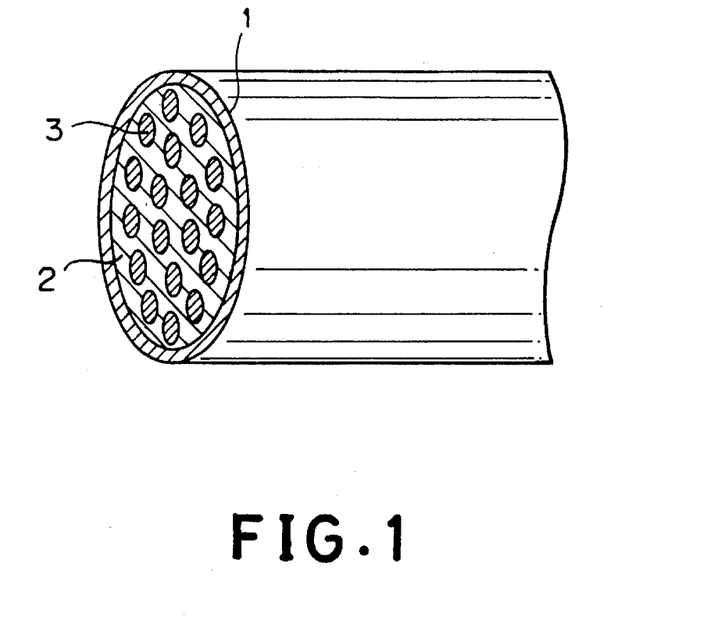
FIG. 1 is a perspective view showing the outlined structure of a sensor electrode using a bundle of linear thin carbon member in accordance with the present invention.

The carbon sensor electrode using a composite carbon material of the present invention, as FIG. 1 shows its outlined structure, comprises an insulating tube 1 as an insulating tubular member, a reactive substance 2 held inside, and carbon of varying shapes and types as an electrode material 3 penetrating through the reactive substance 2. The reactive substance 2 is a substance which reacts chemically with a composition which is measured by the carbon sensor electrode, such as an active enzyme, a metabolite, a complex ion, an acid, an alkali, a dissolved gas or an organic substance. The top opening of the tube 1 is sealed, or the reactive substance 2 held inside the tube 1 is coexistent with a retaining material such as vaseline, glycerin, oil, paraffin, agar or gelatin so that the reactive substance 2 does not drain into the bulk solution immediately during the reaction. A tip portion of the tube 1 may be covered with an ion exchange membrane with a low electric resistance or a conductive polymeric membrane to prevent the solution from draining. Furthermore, a reaction solution feeder such as a syringe (not shown) may be connected with a base end portion of the tube 1 so that a fresh reaction solution will be constantly fed to the tip of the electrode even if an outflow of the solution occurs.

The carbon sensor electrode can be produced in a simple manner.

In case of the retaining substance being agar, a first process for production comprises dipping the electrode material 3, say, made of a bundle of carbon fibers in a hot solution of the reactant 2 dissolved suitably together with agar to wet the peripheral portion of the electrode material 3 sufficiently with the reactive substance 2; and then passing the electrode material 3 through the tube 1 as such or with the use of a needle-like guide. This will result in a sensor in which at room temperature the reactive substance does not flow out because of the viscous retaining substance.

A second process for production comprises sucking a hot solution of the reactive substance 2, dissolved together with the retaining substance, into the insulating tube 1 attached to the tip of a pipette; inserting a carbon material, which will serve as the electrode material 3, into the solution; and bringing it up and down therein to wet the surface of the electrode sufficiently with the reactive substance 2. When the reactive substance varying in characteristics upon heating is to be handled, the solution of the reactant is introduced at room temperature by any of the above-described methods, whereafter the tip portion of the tube 1 may be covered with an ion exchange membrane with low electric resistance or a conductive polymeric membrane to prevent the outflow of the solution.

The tip of the carbon sensor electrode that has been used once is snapped or cut off, and a fresh electrode surface is used without fail. This will give results with high reproducibility.

In the substantial absence of the retaining substance (carrier), the top opening of the tube 1 including the electrode is sealed, or a solution injector or a pump capable of fine adjustment for a low speed is connected with the tube 1 to produce a slightly negative pressure therein and hold the reactive substance-containing solution around the electrode. This will make the product usable as a sensor.

The carbon sensor electrode of the present invention with the above-described construction is a long-life one comprising an insulating tubular member, a reactive substance such as an enzyme accommodated inside, and carbon fibers as an electrode. Since the tip of the electrode can be easily removed, a fresh sensor electrode surface can be easily provided, thus making the carbon sensor electrode of the invention highly practical. In the carbon sensor electrode, the carbon electrode consists of a bundle of many linear thin carbon members such as carbon fibers and thin carbon rods, and each of the linear thin carbon members are separated by the solution including a reactive substance which reacts chemically with a composition being to be measured by the carbon sensor electrode. Both the carbon member and the solution are an electric conductor, but an electric conductivity of the carbon member is greater than that of the solution. Therefore, in the carbon sensor electrode, low-voltage current in each of the carbon member, which is generated by a reaction between the reactive substance and a composition which is measured by the present carbon sensor electrode, does not flow out to another carbon member through the solution, the current in each of the carbon member flows only in the same carbon member. Thus, the carbon sensor electrode consisting of a bundle of many linear thin carbon member can measure lower voltage current than the current measured by the carbon sensor electrode consisting of one carbon member.

The present embodiment will be described in greater detail below.

Figure 2:
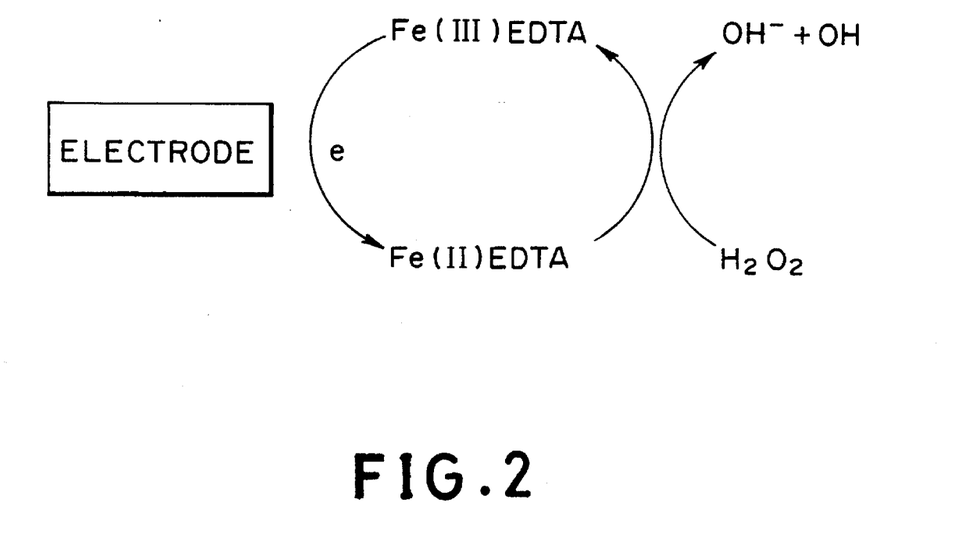
FIG. 2 is a conceptual view illustrating the reaction in the sensor electrode.

Iron-EDTA complex ions serving as an imitation peroxidase were placed in an insulating silicone tube with an inner diameter of 1 mm. A bundle of mechanical pencil leads with a diameter of 0.2 mm was inserted as an electrode material into the tube to obtain a sensor electrode. This sensor electrode was used to detect hydrogen peroxide present in a bulk solution. This reaction proceeds catalytically according to the following formulae, and thus has increased sensitivity and selectivity. A conceptual view of this reaction is shown in FIG. 2.

$$Fe(III)EDTA + e \rightarrow Fe(II)EDTA \tag{I}$$

$$Fe(II)EDTA + H_2O_2 \rightarrow Fe(III)EDTA \tag{II}$$

The reaction of formula (I) proceeds stably in the pH range of from 3.5 to 5 where an acetate-buffer solution is used. In this pH range, the reaction of formula (II) is much faster than the reaction of formula (I). In the presence of hydrogen peroxide, it is an enzyme-like reaction in which Fe(III)EDTA is reproduced instantaneously.

The reaction of formula (I) can be detected by voltammetry as an Iron-EDTA wave at about −0.3 V vs. SCE (slightly different according to pH). If hydrogen peroxide is present, its wave height increases with increasing amount of hydrogen peroxide, thus making the detection of hydrogen peroxide possible. At this time, if there is dissolved oxygen in the solution, oxygen also performs a similar reaction to the reaction of formula (II). Hence, oxygen contained in the solution should be removed before insertion of the present sensor electrode by blowing an inert gas or the like for about 10 minutes beforehand. The tip of the instant sensor electrode was cut off with scissors, and the detection of hydrogen peroxide was attempted repeatedly. The relative standard deviation for the height of the Iron-EDTA reduction wave was 4.6% upon ten repeats of measurements.

Embodiment 2

Figure 3:
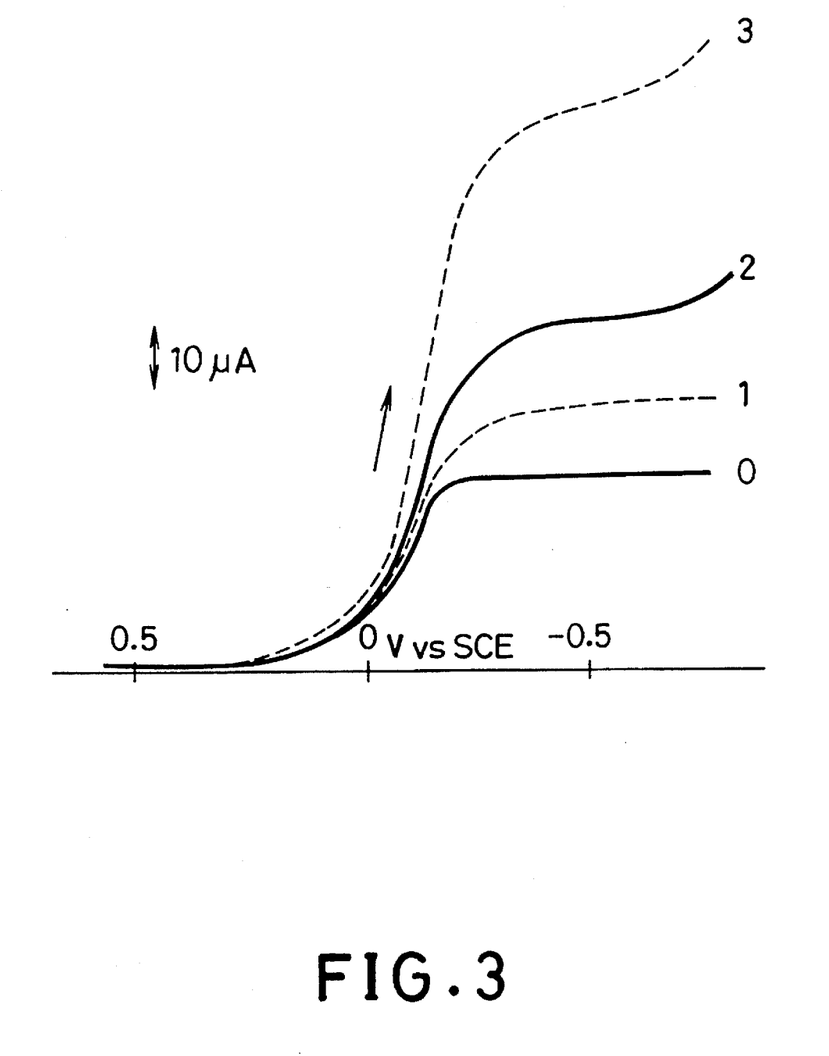
FIG. 3 is linear sweep voltammograms (LSV) of the results of the reaction in the sensor electrode.

In many natural enzyme reactions, hydrogen peroxide is generated after completion of the reaction. Thus, the progress of the enzyme reaction can be estimated by measuring the content of hydrogen peroxide in the reaction solution. In the present invention, the final objective is a sensor electrode of the present construction incorporating peroxidase contained in natural wasabi (a Japanese horseradish). However, the use of Iron-EDTA utilized in Embodiment 1 facilitates the detection of hydrogen peroxide as described above. When attempt is made to detect 1 to 5 mM of hydrogen peroxide present in the solution at pH 4.5, the results shown in FIG. 3 were obtained, confirming the high characteristics of the sensor electrode of the present invention. Curve 0 is a linear sweep voltammogram (LSV) only by Iron-EDTA in the sensor. Curve 1 is an LSV obtained when Iron-EDTA was present together with 0.75% $H_2O_2$. Curve 2 is an LSV obtained when Iron-EDTA was present together with 1.0% $H_2O_2$. Curve 3 is an LSV obtained when Iron-EDTA was present together with 1.5% $H_2O_2$.

Embodiment 3

Figure 4:
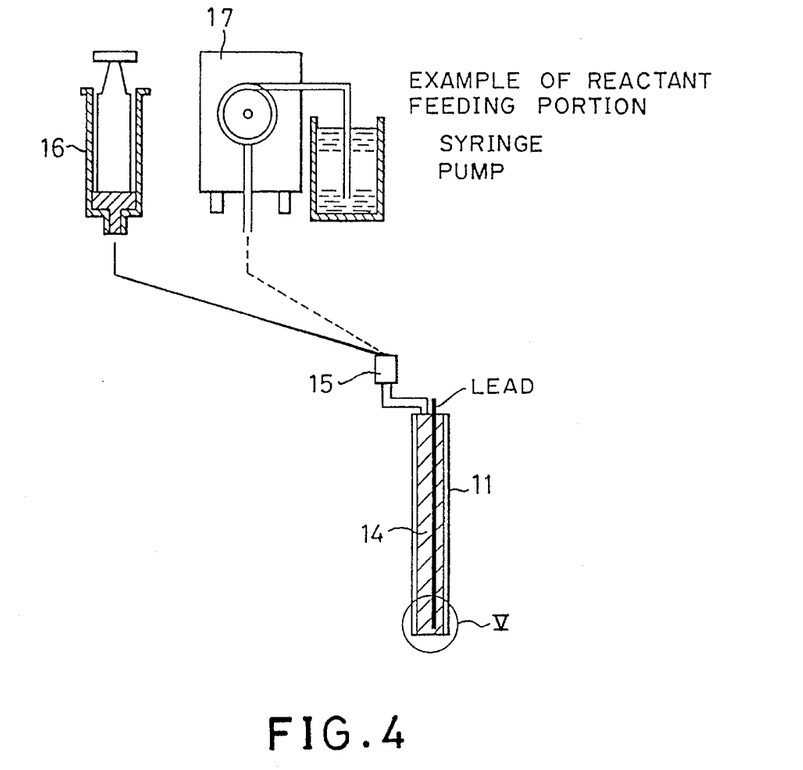
FIG. 4 is a simplified block diagram showing the sensor electrode using a carbon paste in accordance with the present invention.
Figure 5:
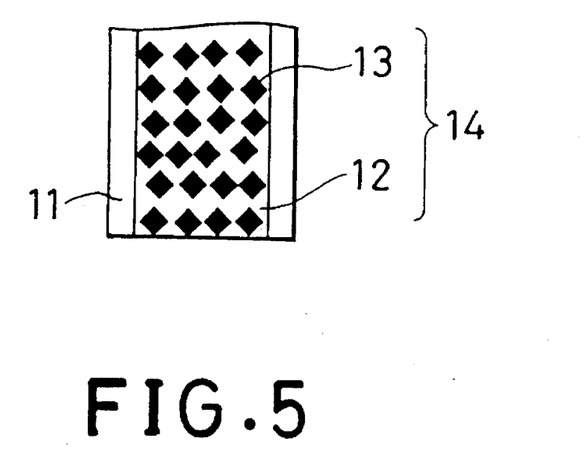
FIG. 5 is an enlarged constructional view showing the portion II in FIG. 4.

The carbon sensor electrode using a carbon paste of the present invention, as FIG. 4 shows its outlined structure, has an insulating tube as an insulating tubular member 11. As shown in FIG. 5, this tube is charged with a carbon paste 14 formed by mixing a reactive substance 12, a carbon material 13 and a retaining substance (carrier). This electrode is either used with the sensor portion facing upward, or used as a suspension type.

Examples of the reactive substance 12 are organic substances including active enzymes, nitrogen metabolites such as uric acid, amino acid metabolites, neurotransmitters such as dopamine, vitamins, organic acids such as acetic acid or citric acid, amines, alcohols, and medicines such as anesthetics; complex ions; inorganic acids such as hydrochloric acid or sulfuric acid; alkalis such as ammonia or hydroxides; salts of the inorganic acids and alkalis; soluble gases such as oxygen, chlorine or nitrogen oxides; mixtures of any of these; and substances containing any of them.

To prevent any such reactive substance 12 from immediately draining into the bulk solution during the reaction, the reactive substance 12 may be present together with a carrier such as vaseline, glycerin, oil, paraffin, agar or gelatin.

Furthermore, a tip portion of the tube may be covered with an ion exchange membrane with a low electrical resistance, a conductive polymeric film, or a dialysis membrane in order to prevent the outflow of the solution.

A method of preparing this electrode comprises mixing the reactive substance 12 thoroughly with the carbon material 13 (comprising fine carbon particles or short carbon fibers) as a dispersion in water or an organic solvent along with vaseline, glycerin, oil, paraffin, agar or gelatin for holding the reactive substance 12 in place so as to prevent its immediate outflow into the solution. This mixing results in the formation of a carbon paste 14. Then, this carbon paste 14 is pushed into an insulating tube (tubular member 11) using a piston or the like, or is rolled in a sheet of an insulating film (tubular member 11).

With the electrode of the present invention, a sensor free from outflow of the reactive substance can be constructed because of the viscous retaining substance.

With the carbon electrode of the present invention, moreover, the sensor portion (tip of the electrode) once used is snapped or cut off, and a fresh electrode surface must be used without fail; alternatively, the paste in the tip portion that has been used is pushed off to supply a fresh electrode surface, whereby highly reproducible results can be obtained.

Even in the substantial absence of the retaining substance, a piston or the like is connected with the tube to produce a slight negative pressure in it, thereby holding the paste in the tube so that it can be used as a sensor.

In the carbon electrode of the present invention, furthermore, as illustrated in FIG. 4, an end (base end) of the tube 11 is provided with a connecting port 15. A piston (syringe) 16 or a pump 17 is connected with the connecting port 15 via a tube (not shown) in order to feed a fresh carbon paste.

In the above-described construction, an enzyme or the like kneaded with carbon in a paste form using a solvent for preventing dispersion in the solution may be extruded to give a fresh carbon paste surface, thereby providing a carbon paste suspension type electrode or carbon paste disk electrode having a fresh electrode surface.

The carbon sensor electrode of the present invention with the above-mentioned construction has a structure in which a carbon paste containing thin carbon materials as an electric lead and preferably containing a reactant such as an enzyme is housed inside an insulating tubular member, and a tip portion degraded upon use is extruded and can be easily removed. Hence, the carbon sensor electrode can easily provide a fresh sensor electrode surface for a long term, thus ensuring highly practical use.

The present embodiment will be described in more detail below.

To graphite particles (mechanical pencil lead powder) was added liquid paraffin in an amount of 35% based on the amount of the graphite particles. The particles were thoroughly dispersed, and the mixture kneaded. Then, the resulting paste was poured into a syringe without a needle, and injected into an open-ended silicone tube with a diameter of 1.5 mm by means of the piston of the syringe.

An end of the tube with the paste fully introduced was cut off, and the surface of the electrode was flattened with a smooth sheet such as a waxed paper. Then, a dialysis membrane (Union Carbide) cut in a round shape with a slightly larger size than the electrode surface was placed on the tip of the tube, and fixed in place with an O-ring.

Figure 6:
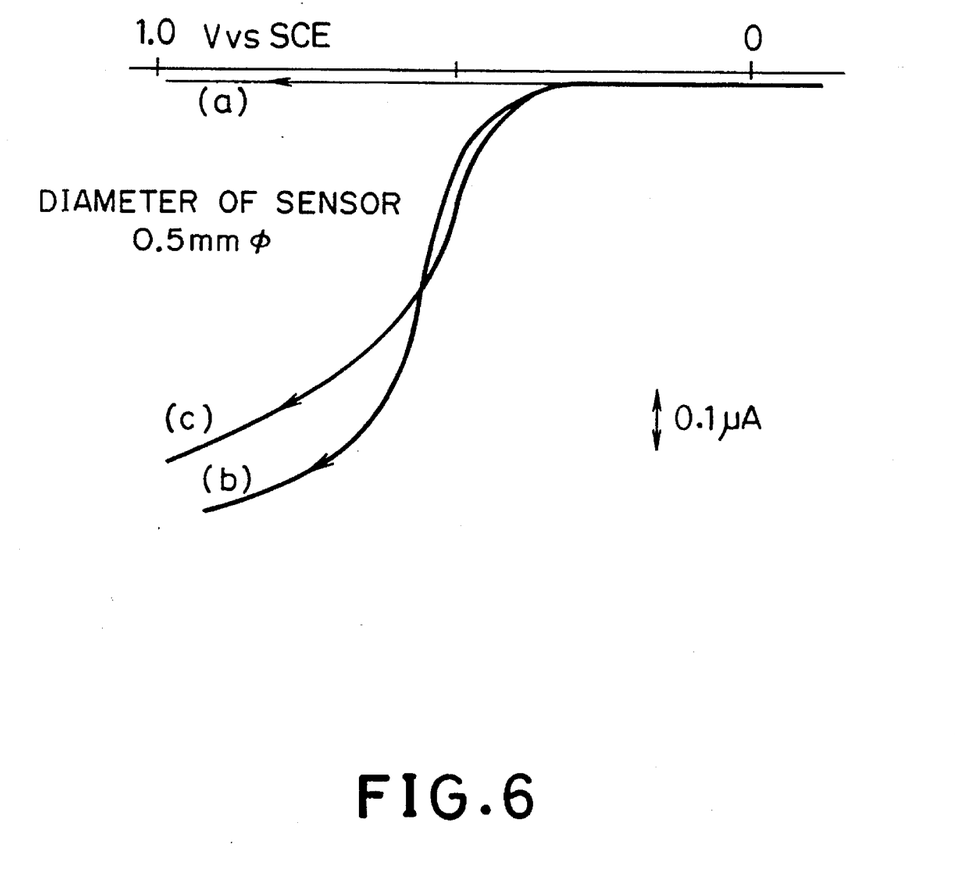
FIG. 6 is voltammograms of uric acid in the sensor electrode using a carbon paste in accordance with the present invention without a built-in reactive substance.

This electrode was used to detect uric acid in urine. Generally, the pH of human urine is about 6.5, and so a known amount of Ringer's solution adjusted to pH 6.5 containing a certain volume of human urine was used as an assay system. Lactam-type uric acid has three quinone groups (—C=O), one of which produces a rapid electrode reaction with the hydroxyl group —OH of the lactim form based on a redox reaction, thus showing an easily observable redox wave. Its redox potential is about 0.5 V vs. SCE at that pH, and reduction waves are at much more negative potentials. The results are given in FIG. 6. With the background Ringer's solution, no waves were observed as in (a) of the drawing. When 50 μg uric acid was contained in 1 ml of the solution, the curve (b) was obtained. The results (c) with uric acid in human urine were slightly less than in (b). The preparation of a calibration curve would make assay easy. When the electrode was dipped for more than about 5 minutes, the wave heights gradually decreased, probably because other ingredients in the urine may have been adsorbed to it. Since the adsorbate cannot be removed without potent oxidation, the paste electrode at the tip of the electrode once used should be cut off or extruded off, and next assay should be performed with a fresh electrode surface. Upon addition of much uric acid to human urine, sediments occur, hindering assay.

Embodiment 4

In many natural enzyme reactions, hydrogen peroxide is generated after completion of the reaction. Thus, the progress of the enzyme reaction can be estimated by measuring the content of hydrogen peroxide in the reaction solution. In the present invention, the final objective is a sensor electrode of the present construction incorporating peroxidase contained in naturally occurring wasabi (a Japanese horseradish). Instead, the use of Iron-EDTA facilitates the detection of hydrogen peroxide, because of an electrochemical catalytic reaction as illustrated in FIG. 2.

Therefore, an imitation enzyme having Iron-EDTA saturated in an 80% aqueous solution of glycerin was kneaded with carbon, and the detection of hydrogen peroxide in a solution was attempted using this kneaded product. In detail, graphite particles (mechanical pencil lead powder) were thoroughly dispersed and kneaded in an 80% aqueous solution of glycerin (Wako Junyaku). Then, the resulting paste was poured into a syringe without a needle, and injected into an open-ended tube with a diameter of 0.5 mm by means of the piston of the syringe to prepare a carbon sensor electrode with a built-in imitation enzyme.

Figure 7:
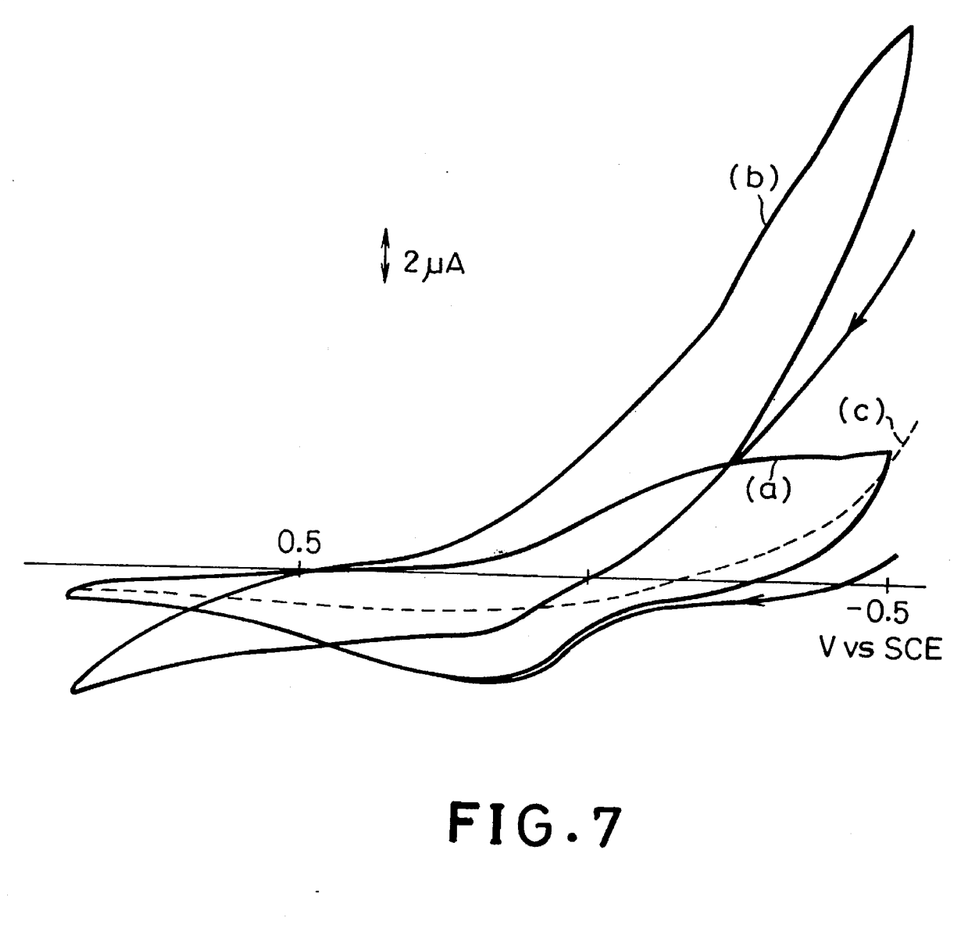
FIG. 7 is a graph showing cyclic voltammograms of iron-EDTA by the sensor electrode using a carbon paste in accordance with the present invention, as well as the results of detection of hydrogen peroxide by the sensor electrode.

This electrode was used to detect 0.03% by volume of hydrogen peroxide present in acetate buffer solution (pH 5.5). The results are shown in FIG. 7. A curve (a) is a voltammogram of iron-EDTA determined by the Fe-EDTA-incorporated sensor electrode. A curve (b) is a voltammogram obtained in the solution containing 0.03% hydrogen peroxide with the use of this sensor electrode. One can clearly observe wave heights increasing because of hydrogen peroxide.

The detection of 0.03% by volume of hydrogen peroxide was attempted using the paste electrode without Fe-EDTA. The results are revealed as a curve (c).

As described above, the reactive substance-incorporated carbon sensor electrode of the embodiment provides a disposable carbon sensor electrode suitable for in situ measurement of specific substances in many biological samples which has been infeasible for long with conventional sensors or sensor electrodes.

Specifically, the carbon sensor electrode using a carbon paste in accordance with the present invention serves as a practical sensor electrode which comprises a carbon paste incorporating a reactant such as an enzyme in an insulating tube. It has a structure capable of long-term use and can easily provide a fresh sensor electrode surface when its tip is either snapped or cut off, or extruded.

Moreover, the carbon sensor electrode using a composite carbon material in accordance with the present invention serves as a practical sensor electrode which comprises carbon fibers or the like incorporating a reactant such as an enzyme in an insulating tube. It has a structure capable of long-term use and can easily provide a fresh sensor electrode surface when its tip is either snapped or cut off.

Embodiment 5

Figure 8:
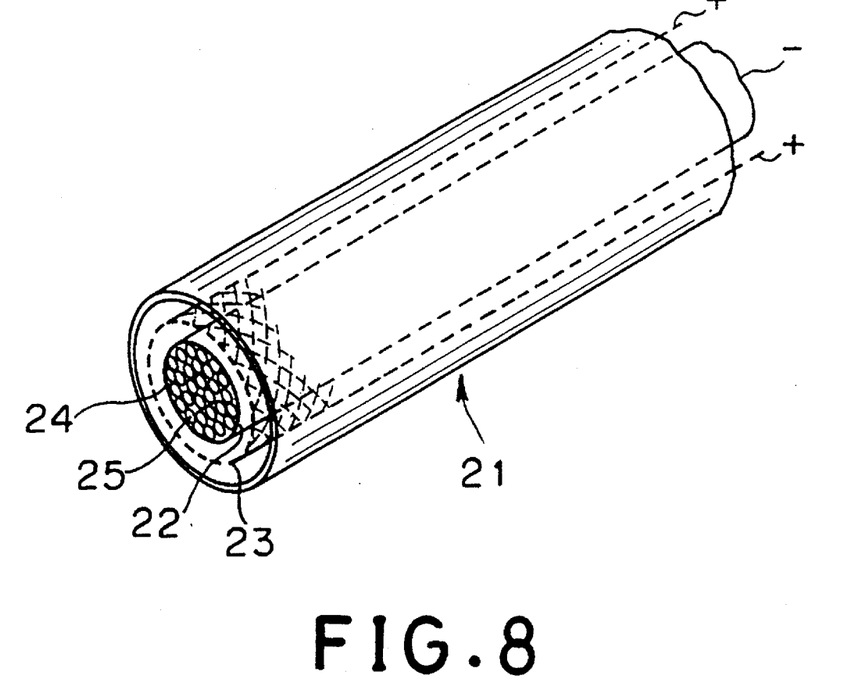
FIG. 8 is a simplified structural view showing a redox type carbon sensor electrode in accordance with the present invent ion.

A carbon sensor electrode of this embodiment is a redox type sensor electrode. The redox type carbon sensor, as schematically shown in FIG. 8, comprises an insulating tubular member 21, a cylindrical ion permeable membrane 22 disposed inside the tubular member 21, a second carbon electrode 23 of a cylindrical shape disposed between the ion permeable membrane 22 and the tubular member 21, a reactive substance-containing solution 24 held inside the ion permeable membrane 22, and a first carbon electrode 25 penetrating through the ion permeable membrane 22.

Examples of the first and second carbon electrodes 25 and 23 are various carbon materials of various shapes, such as twisted yarns of carbon fibers, bundles of twisted carbon yarns, cloths of twisted carbon yarns, thin carbon rods, or bundles of thin carbon rods.

The twisted yarn of carbon fibers, bundle of carbon fibers or twisted carbon yarns, carbon cloth, thin carbon rod, or bundle of thin carbon rods can be used as the second carbon electrode 23 in the tube in order to prevent the reactive substance, i.e. active enzyme, metabolite, complex ions, acid, alkali, dissolved gas, or other organic matter, from becoming deactivated in the redox carbon sensor electrode. This carbon electrode is characterized in that the reactive substance can be kept in an appropriate environment and its function preserved by applying a suitable potential between the second carbon electrode 23 and the first carbon electrode 25 by means of a battery or the like so that the reactive substance may not be deactivated during storage in the sensor.

The ion permeable membrane 22 is an ion exchange membrane, an ion permeable membrane of cellophane or the like, a sintered glass membrane, or an insulating ion permeable membrane of a Teflon filter paper or the like.

The insulating tubular member 21 is an insulating tube or an insulating sheet rolled into a tubular form.

The reactive substance which reacts chemically with a composition being to be measured by the carbon sensor electrode may be one containing a substance such as an active enzyme, a metabolite, complex ions, an acid, an alkali, or a dissolved gas.

In the above-described construction, the reactive substance can be coexistent with a retaining material such as vaseline, glycerin, oil, agar or gelatin, or an ion permeable membrane can be attached to a front end of the tubular member, in order to prevent the reactive substance from draining immediately into the bulk solution.

Figure 9:
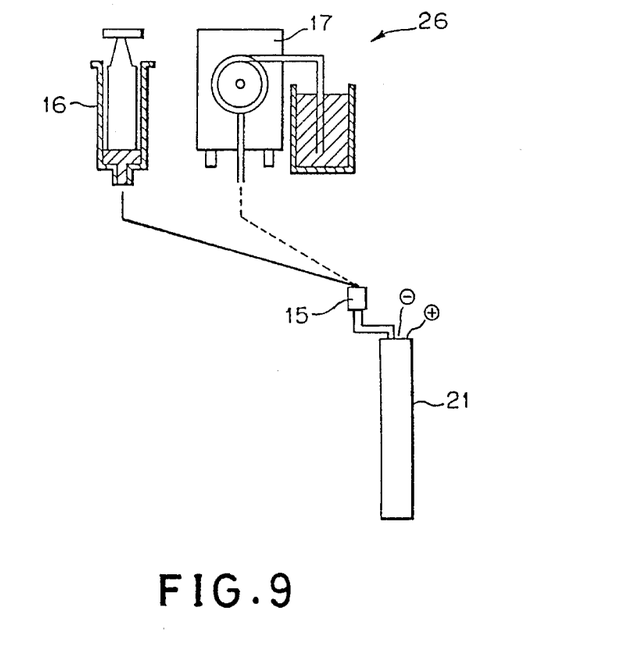
FIG. 9 is a simplified structural view showing the redox type carbon sensor electrode in accordance with the present invention connected to a reaction solution feed mechanism.

In the redox type carbon sensor electrode, a reaction solution push-out mechanism 26 capable of constantly feeding a reaction solution into the electrode is provided if desired, as illustrated in FIG. 9. The reaction solution push-out mechanism 26 may be a syringe 16 or a fixed quantity feed pump 17. In this case, a connecting port 15 is provided at a base end of the tubular member 21. The syringe 16 or pump 17 is connected with the connecting port 15 via a tube (not shown) to feed a fresh reaction solution.

A process for producing the carbon sensor electrode can be performed relatively simply.

First of all, a carbon material of a varying shape and type (second carbon electrode 23) is disposed between the inside wall of the insulating tubular member 21 and the ion permeable membrane 22. A hot solution of a supporting electrolyte and a retaining material is poured between the inside wall of the second carbon electrode 23 and the ion permeable membrane 22. Then, an electrode made of a bundle of twisted carbon yarns as the first carbon sensor electrode 25, for example, is dipped in a hot solution of a reactive substance dissolved suitably together with the supporting electrolyte and the retaining material to wet the peripheral portion of the electrode 25 sufficiently with the reactive substance. Then, the electrode 25 is passed through the cylindrical ion permeable membrane 22 as such or with the use of a needle-like guide. This results in a carbon sensor electrode in which the reactive substance inside the electrode does not flow out because of the supporting electrolyte and the retaining material showing viscosity at room temperature.

Another process for production comprises attaching a cylindrical ion permeable membrane 22 to the tip of a pipette, handling the pipette to suck into the ion permeable membrane 22 a hot solution of the reactive substance having the supporting electrolyte and the retaining material dissolved together with it, inserting a carbon material, which will serve as the first carbon electrode 25, into the solution, and moving the carbon material up and down therein to wet the surface of the electrode 25 sufficiently with the reactive substance. Then, a desired carbon sensor electrode is assembled in the same manner as in the aforementioned first process.

When the reactive substance varying in characteristics upon heating is to be handled, the solution is introduced at room temperature into the tubular member 21 by one of the above-described methods, whereafter the tip portion of the tubular member 21 may be covered with an ion exchange membrane with low electric resistance or a conductive polymeric membrane to prevent the outflow of the solution from the inside.

With the carbon sensor electrode of the foregoing construction, when the sensor is to be used again after being used once, the used portion of the electrode must be snapped or cut off to expose a fresh electrode surface. This will give the results of measurement with high reproducibility. In this case, a fresh reaction solution needs to be fed to the tip of the electrode. Thus, it is preferred to provide the insulating tubular member 21 with the reaction solution push-out mechanism 26 capable of constantly feeding a reaction solution.

The present embodiment will be described in greater detail below.

In a redox type carbon sensor electrode of a structure as illustrated in FIG. 8, a silicone tube with an inside diameter of 5 mm was used as an insulating tubular member 21. A cylindrical cellophane was inserted as an ion permeable membrane 22 into the silicone tube. Between the cellophane cylinder and the silicone tube, acetic acid-sodium acetate buffer was filled, and a number of mechanical pencil leads with a diameter of 0.5 mm were arranged in an annular form as a second carbon sensor electrode 23. Then, iron-EDTA complex ions serving as an imitation peroxidase were placed in the ion permeable membrane 22, i.e. the cellophane cylinder. A bundle of mechanical pencil leads with a diameter of 0.2 mm was further inserted as a first carbon sensor electrode 25 into the cylinder. Finally, an electric source such as a battery (not shown) was connected between the second carbon electrode 23 and the first carbon electrode 25 so that a suitable potential would be applied.

In the so constructed redox type carbon sensor electrode, a suitable potential was applied between the second carbon electrode 23 and the first carbon electrode 25, and hydrogen peroxide present in the iron-EDTA bulk solution was detected, with the ion valence of the iron in the iron-EDTA complex ions being kept at 2. Since this reaction, as well as described above, proceeds catalytically according to the following formulae, it has increased sensitivity and selectivity.

$$Fe(III)EDTA + e \rightarrow Fe(II)EDTA \quad (I)$$

$$Fe(II)EDTA + H_2O_2 \rightarrow Fe(III)EDTA \quad (II)$$

The reaction of formula (I) proceeds stably in the pH range of from 3.5 to 5 where an acetate buffer solution is used.

In this pH range, the reaction of formula (II) is much faster than the reaction of formula (I). In the presence of hydrogen peroxide, it is an enzyme-like reaction in which Fe(III)EDTA is reproduced instantaneously. As mentioned set forth, a conceptual view of this reaction is given as FIG. 2.

The reaction of formula (I) can be detected by voltammetry as an Iron-EDTA wave at about −0.3 V vs. SCE (slightly different according to pH). If hydrogen peroxide is present, its wave height increases with increasing amount of hydrogen peroxide, thus making the detection of hydrogen peroxide possible. At this time, if there is dissolved oxygen in the solution, oxygen also performs a similar reaction to the reaction of formula (II). Hence, oxygen contained in the solution should be removed before insertion of the present carbon sensor electrode into the bulk solution by blowing an inert gas or the like in the solution for about 10 minutes beforehand.

Figure 10:
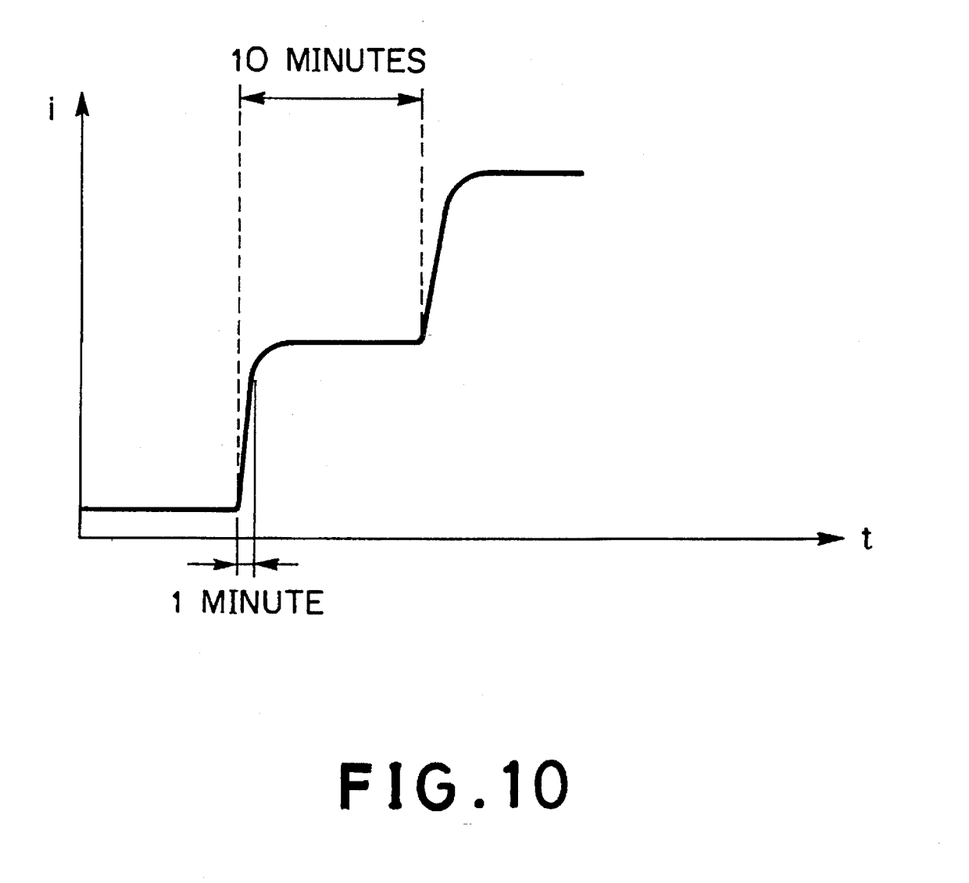
FIG. 10 is a graph illustrating the response curve of hydrogen peroxide in the redox type carbon sensor electrode of the present invention using Fe(II)EDTA as a reactive substance.

Then, the tip of the carbon sensor electrode was cut off with scissors, and the detection of hydrogen peroxide was attempted repeatedly. As shown in FIG. 10, the response rate (rise time) was about 1 minute, demonstrating a response in linear relationship with the amount of hydrogen peroxide present. The total response time was 10 minutes.

As described above, the present invention can provide a satisfactory carbon sensor electrode which is suitable for the in situ measurement of specific substances in many biological samples, and which can take the place of conventional carbon sensor electrodes whose long-term use has been impossible.

Specifically, the carbon sensor electrode of the present invention is a reactant-incorporating, carbon-based sensor electrode capable of long-term use which has in an insulating tubular member a storage mechanism for a reactive substance which should be kept to be of an oxidation or reduction type (redox type). Since its tip portion is removable, moreover, it can easily provide a fresh sensor electrode surface. Thus, it serves as a practical sensor electrode.

The present invention has been described in detail with respect to preferred embodiments, and it will now be obvious that changes and modifications may be made without departing from the invention in its broader aspects, and it is our intention, therefore, in the appended claims to cover all such changes and modifications as fall within the true spirit of the invention.

What is claimed is:

1. A carbon sensor electrode, comprising:
   an insulating tubular member having a base end and a tip end in which is defined an opening;
   a carbon electrode consisting of a bundle of a plurality of carbon members which are linear and thin, which are disposed in the insulating tubular member, and each one of which plurality of carbon members extends from the base end of the insulating tubular member to the tip end of the insulating tubular member; and
   a solution containing a reactive substance which reacts chemically with a composition which is measured by the carbon sensor electrode, and positioned between the carbon electrode and the insulating tubular member, and between each of the plurality of carbon members.

2. The carbon sensor electrode as claimed in claim 1, wherein the plurality of carbon members are carbon fibers.

3. The carbon sensor electrode as claimed in claim 1, wherein the plurality of carbon members are thin carbon rods.

4. The carbon sensor electrode as claimed in claim 1, wherein the solution containing the reactive substance is mixed with a carrier and held in place.

5. The carbon sensor electrode as claimed in claim 4, wherein the solution mixed with the carrier is further mixed with a fine carbon material to produce a carbon paste, and the carbon paste is filled between the carbon electrode and the insulating tubular member, and between each of the plurality of carbon members.

6. The carbon sensor electrode as claimed in claim 1, wherein the opening defined in the tip end of the insulating tubular member is sealed with a membrane selected from the group consisting of an ion permeable membrane, an ion exchange membrane, and a dialysis membrane.

7. The carbon sensor electrode as claimed in claim 1, further comprising a reaction solution feeder for feeding the solution containing a reactive substance into the insulating tubular member, which is connected with the base end of the insulating tubular member.

8. A carbon sensor electrode, comprising:

an insulating tubular member having a base end and a tip end in which is defined an opening; and a carbon electrode consisting of a carbon paste positioned inside the insulating tubular member and extending continuously from the base end to the tip end, which carbon paste comprises at least a fine carbon material, a carrier, and a solution containing a reactive substance which reacts chemically with a composition which is measured by the carbon sensor.

9. The carbon sensor electrode as claimed in claim 8, wherein the opening defined in the tip end of the insulating tubular member is sealed with a membrane selected from the group consisting of an ion permeable membrane, an ion exchange membrane, and a dialysis membrane.

10. The carbon sensor electrode as claimed in claim 8, further comprising a carbon paste feeder for continuously feeding the carbon paste into the insulating tubular member, the carbon paste feeder being connected with the base end portion of the insulating tubular member.

11. A carbon sensor electrode, comprising:

an insulating tubular member having a base end, and a tip end in which is defined an opening;

an ion permeable membrane which is cylindrical and which is disposed in the insulating tubular member;

a first carbon electrode which is disposed in the ion permeable membrane;

a solution containing a reactive substance which reacts chemically with a composition which is measured by the carbon sensor electrode, and positioned on the first carbon electrode and between the first carbon electrode and the ion permeable membrane; and a second carbon electrode which is disposed between the insulating tubular member and the ion permeable membrane.

12. The carbon sensor electrode as claimed in claim 11, wherein the first carbon electrode consists of a bundle of a plurality of carbon members which are linear and thin.

13. The carbon sensor electrode as claimed in claim 11, wherein the first carbon electrode is composed of one member selected from the group consisting of a twisted carbon yarn of carbon fibers, a thin carbon rod, a bundle-form carbon composed of twisted carbon yarns or thin carbon rods, and a carbon cloth of twisted carbon yarns.

14. The carbon sensor electrode as claimed in claim 11, wherein the second carbon electrode is composed of one member selected from the group consisting of a twisted carbon yarn of carbon fibers, a thin carbon rod, a bundle-form carbon composed of twisted carbon yarns or thin carbon rods, and a carbon cloth of twisted carbon yarns.

15. The carbon sensor electrode as claimed in claim 11, wherein an ion permeable membrane is attached to the tip end of the tubular member so that the reactive substance does not immediately drain into the solution which is measured.

16. The carbon sensor electrode as claimed in claim 11, further comprising a reaction solution push-out mechanism, which constantly feeds the reaction solution, attached to the insulating tubular member.

* * * * *